United States Patent [19]

Lu et al.

[11] Patent Number: 4,720,508

[45] Date of Patent: Jan. 19, 1988

[54] HALOGENATED SATURATED HYDROCARBONS AND SATURATED HYDROCARBON IN COMBINATION AS ACARICIDAL COMPOUNDS

[75] Inventors: Jing-Jong Lu; Radmilo A. Todorovic, both of Terre Haute, Ind.

[73] Assignee: International Minerals & Chemical Corp., Terre Haute, Ind.

[21] Appl. No.: 940,753

[22] Filed: Dec. 11, 1986

Related U.S. Application Data

[62] Division of Ser. No. 789,100, Oct. 18, 1985, Pat. No. 4,657,936.

[51] Int. Cl.$^4$ .................... A01N 27/00; A01N 29/02

[52] U.S. Cl. ..................... 514/758; 514/762
[58] Field of Search .................. 514/758, 762

[56] References Cited

FOREIGN PATENT DOCUMENTS 54-20135  2/1979  Japan .................. 514/758

*Primary Examiner*—Allen J. Robinson
*Attorney, Agent, or Firm*—W. R. Guffey; T. L. Farquer

[57] ABSTRACT

The invention relates to acaricidal compositions for the control of ectoparasites of domesticated, warm blooded animals. Methods for application of the composition disclosed are also taught.

4 Claims, No Drawings

HALOGENATED SATURATED HYDROCARBONS AND SATURATED HYDROCARBON IN COMBINATION AS ACARICIDAL COMPOUNDS

This application is a division of application Ser. No. 789,100, filed Oct. 18, 1985, now U.S. Pat. No. 4,657,936.

BACKGROUND OF THE INVENTION

The present invention relates to acaricidal compositions, and to methods of use of the compositions to control acarid pests.

Ectoparasites of the genus Acarina, for example ticks, affect cattle, sheep, domestic pets, plants and humans. Many are parasitic, harming the host organisms by appropriating nutrients and metabolites for their own use. In addition, many acarids are vectors for the transmission of diseases, such as tick paralysis and tick toxicosis, sweating sickness, babesiosis (Texas Fever), anaplasmosis, theileriosis and heart water. Such diseases can cause death, morbidity, damaged hides, loss in growth rate, reduction in milk production, and reduction in quality of meat. Thus, acarids can pose a large economic problem in the raising of livestock.

Some acarids, for example cattle ticks, are capable of surviving on grasses in the fields for long periods of time, in the absence of their host animals. The ticks are negatively geotropic, and climb up the grasses. When the host animals are present, the ticks are transferred to them by contact with the grasses. To eliminate ticks from infested pasture land, fields may be burned, crops cultivated, or the fields may be kept free of animals for a number of years. Alternatively, the fields can be treated with chemicals which either kill the ticks or immobilize them. Yet another method is to topically apply chemicals which kill the ticks to the host animals themselves.

Various chemicals have been developed for use against ticks. However, these chemicals lose their efficacy after a period of widespread use due to the spread of resistance among the tick population. For example, arsenic was used to control tick populations from the early 1900's, but prior to World War II the Boophilus spp. ticks developed resistance to arsenic. Later, the organochlorines, DDT, BHC and toxaphene were used to control the arsenic-resistant tick populations. Resistance and unacceptable accumulation of toxic organochlorine residues in meat led to their replacement with organophosphorous and carbamate compounds. These chemicals were then supplanted by formamidines. Because of the seemingly limitless ability of populations to acquire resistance and the dependence of the cattle industry on tick control agents (acaricides) there is a continuing need for new compounds to replace those in the arsenal which are no longer effective.

SUMMARY OF THE INVENTION

It is an object of the invention to provide a composition for killing acarids.

It is an object of the invention to provide a method for treating animals to eliminate and prevent infestation by acarids.

It is a further object of the invention to provide a method for killing acarids.

In accordance with the above objects an acaricidal composition is provided comprising at least one compound selected from the group consisting of: 1-chloroundecane, octadecane, 1-chlorooctadecane, 1-chlorotetradecane, 1,2-epoxycyclododecane, 1,2-epoxyoctadecane, 1-chlorohexadecane, cis-oleylamine and undecanoic acid. In addition, methods are provided for using the acaricidal compositions to kill ticks, and for applying the composition to animals and the tick habitat.

DESCRIPTION OF THE INVENTION

The compositions of the present invention have been shown to be effective in killing ticks. They are active against ticks at various stages of the life cycle, including larvae, nymphs, eggs and replete females. The compositions are active against a variety of species including *Amblyomma variegatum, Boophilus microplus,* and *Rhipicephalus sanguineus.*

Any of the compounds can be applied alone or in combination with others. Application is facilitated by applying an effective amount of an acaricidal composition in an inert chemical carrier. Such compositions may take the form of solutions, dispersions, emulsions, dusts, dust concentrates, wettable powders, and the like. Often the compounds will be applied as a solution in a suitable solvent, such as acetone, lower alkanol, toluene, and the like. Solvents should be inert to the active ingredients, not phytotoxic, and preferably odorless. Generally compositions containing concentrations of the active acaricidal compounds between about 1% and about 15% by weight can be used successfully. The active acaricidal compounds can also be used as diluents, stabilizers or carriers for delivery of other pesticides, insecticides and acaricides.

Solid formulations such as dusts or dust concentrates can be prepared by grinding and blending an inert solid diluent with the solid form of the composition of the present invention. Such diluents are well known in the art and include talc, chalk, kaolin, diatomaceous earth, ground corn cob grits, and the like. Alternatively, the liquid form of the composition alone or in a suitable solvent can be sprayed on the inert solid diluent. Dusts generally contain from about 1% to about 15% by weight of an acaricidal composition, while concentrates may contain from about 16% to about 85% of the active composition.

Wettable powders can be prepared as dusts, but contain about 5% to about 10% by weight of an additional surfactant. Adhesives can also be added to the solid formulations, for example, to improve the adhesion of the active ingredients to parts of plants. Examples of suitable additives include: mixtures of chalk and olein, cellulose derivatives (methyl or carboxymethyl), carbowaxes, polyvinyl pyrrolidones and the like.

Compositions may be applied to the ticks directly, to the tick habitat, or to the host animals. Host animals are generally treated by spraying or dipping the animals in a dispersion, paste, emulsion or solution of the active composition. Habitats are generally treated by dusting, for example, from an aircraft, over large areas of vegetation. The composition can also be applied to pasture lands by means of sprinkle, spray or drip irrigation systems. The ticks themselves can be dipped or sprayed or directly contacted with the surface containing the composition or a residue thereof. It is thought that vapors of the composition may be sufficient to kill ticks, even without actual contact.

Host animals may be treated prophylactically, or therapeutically. Prophylactic treatment may be administered regularly at lower dosages than those needed after the animals have already been infested. Host animals can be treated with an acaricidal composition by dipping, spraying, or pourons. Alternatively, legs or ears can be tagged with a slow release device. These techniques are well known in the art.

The following examples are provided to exemplify the foregoing; it is not intended that they limit the scope of the invention.

EXAMPLES

Methods and Materials

A disposable pipette method as described by Koch and Burkwhat, *J. of Econ. Entomol.*, 76: 337-339 (1983), was used to test the effectiveness of residues of compositions for control of three week old larvae of *B. microplus* and seven week old nymphs of *A. variegatum*.

The technical material was dissolved in acetone to formulate dilutions of 15, 7.5, 3.75 and 1.87% weight per volume. Each one ml glass transfer pipette was immersed for one minute in an acetone-technical material dilution, or in pure acetone as a control, in 25 ml graduated cylinders. The treated and control pipettes were then removed from the graduated cylinders and rolled onto paper toweling to dry the outside of each pipette. The pipettes were allowed to further dry for 30 minutes before larvae or nymphs were introduced.

Larvae of *B. microplus* were obtained from colony females that had been collected previously from bovine hosts. The colony of *B. microplus* was originally established from ticks collected from cattle in Puerto Rico in 1981. Nymphs of *A. variegatum* used in these studies were obtained from a colony that was established from ticks collected in Puerto Rico in 1980.

Flat larvae of *A. variegatum* were fed on rabbits and then placed in a rearing chamber at 26° C. and 96% relative humidity, and allowed to molt into flat nymphs. The flat nymphs were allowed to age for seven weeks before being used in these studies.

Larvae of *B. microplus* were prepared by placing three week old larvae in a white enamel pan. The larvae were the progeny of 15 females and were allowed to mix freely in the pans before ten larvae were aspirated into each tube, using a vacuum pump. The larvae were trapped in the pipettes by placing organdy cloth over the large end and securing it with a latex band. After the ten larvae were aspirated into the pipette, the small end of each pipette was sealed with modeling clay.

The larvae-containing, treated and control pipettes were then placed in a rearing chamber at 26° C. and 96% relative humidity for 24 hours. At 24 hours, mortality of larvae was determined. Ticks that did not respond to human breath or did not move when prodded were considered dead.

Nymphs of *A. variegatum* were treated in a similar manner as larvae of *B. microplus*. New acetone-technical material dilutions were prepared at the same concentration levels as described above. The pipettes were immersed and processed identically.

Nymphs from three groups of the same age were mixed together and ten nymphs were dropped into the large end of each treated and control pipette. The small end of each pipette was sealed with modeling clay to prevent tick escape. The large end of each pipette was then sealed with organdy cloth held in place with a latex band.

The nymph-containing treated and control pipettes were then held for 24 hours in a similar rearing chamber as the larvae. Nymphs that did not respond to prodding or human breath were considered dead.

Replete females of *B. microplus* were collected from bovine hosts and weighed. Five females each were dipped for 30 seconds in concentrations of 25, 12.5, 6.25 and 2.75% weight per volume of the 1:1 mixture in acetone. Five ticks were dipped in acetone as controls. The females, after dipping, were allowed to dry five minutes before being placed in glass vials and incubated in a rearing chamber at 26° C., 96% relative humidity, and a 14:10 photophase.

Egg masses laid by treated and control ticks were removed 14 days after treatment. The eggs were weighed and returned to the vials and chamber for hatching. The percentage hatch was estimated visually twenty days after egg masses were weighed. The estimated reproduction (ER) for each female was calculated as follows:

$$ER = (\text{weight of eggs(g)}/\text{weight of female(g)}) \times \% \text{ hatch} \times 20{,}000$$

The factor of 20,000 is a constant and is the estimate of the number of larvae of *B. microplus* in one gram of eggs.

The percent control for each concentration was calculated using Abbott's formula (*J. of Econ. Entomol.*, 18: 265-267 (1925) as follows:

(ER control−ER treated)/ER control×100=% control

EXAMPLE 1

The effects of residues of a 1:1 mixture of octadecane and 1-chloroundecane on three week old larvae of *B. microplus* are presented in Table 1. The mixture provided 100% death of *B. microplus* larvae at 24 hours after exposure at a concentration of 15% weight per volume, and 70% death at a concentration of 1.87% weight per volume.

TABLE 1

| % Concentration | # ticks/ tube | # dead at 24 hrs | % Control |
|---|---|---|---|
| 15 | 10 (5)** | 50 | 100 |
| 7.5 | 10 (5) | 49 | 96.7 |
| 3.75 | 10 (5) | 43 | 76.7 |
| 1.87 | 10 (5) | 41 | 70 |
| Control | 10 (5) | 20 | — |

Effects of residues of 1:1 mixture of octadecane and 1-chloroundecane on 3 week old larvae of a Puerto Rican strain of *Boophilus microplus* (Canestrini)

**Number in parenthesis represents number of replications.

EXAMPLE 2

The effects of residues of the 1:1 mixture of octadecane and 1-chloroundecane on seven week old nymphs of *A. variegatum* are presented in Table 2. The 15% concentration provided death of 86% of the nymphs at 24 hours post-exposure. Similar percentages of death were obtained when 7.5% to 1.87% weight per volume concentrations were used.

TABLE 2

| % Concentration | # ticks per tube | # dead at 24 hrs | % Control |
|---|---|---|---|
| 15 | 10 (5)** | 43 | 86 |
| 7.5 | 10 (5) | 38 | 76 |

Effects of residues of 1:1 mixture of octadecane and 1-chloroundecane on 7 week old nymphs of a Puerto Rican strain of *Amblyomma variegatum* (Fabricius)

TABLE 2-continued

Effects of residues of 1:1 mixture of octadecane and 1-chloroundecane on 7 week old nymphs of a Puerto Rican strain of *Amblyomma variegatum* (Fabricius)

| % Concentration | # ticks per tube | # dead at 24 hrs | % Control |
|---|---|---|---|
| 3.75 | 10 (5) | 39 | 78 |
| 1.87 | 10 (5) | 39 | 78 |
| Control | 10 (5) | 0 | — |

**Number in parenthesis represents number of replications.

EXAMPLE 3

The results of the dip test of the replete females are presented in Table 3. At 25% and 12.5% weight per volume concentrations, 54.8% and 35.9% control respectively was obtained of the control of the eggs of replete females which were dipped. Lower concentrations provided no control of egg hatching.

TABLE 3

Control of *Boophilus microplus* (Canestrini) replete females with 1:1 mixture of octadecane and 1-chloroundecane as determined by the Drummond dip test

| % Concentration | # Ticks dipped | Female wt ($\overline{X} \pm SE$) | # Females laying eggs | Egg mass wt ($\overline{X} \pm SE$) | # egg masses hatching | % Hatch | ER ($\overline{X} \pm SE$) | Control |
|---|---|---|---|---|---|---|---|---|
| 25 | 5 | 0.3356 ± 0.0302 | 4 | 0.0876 ±0.0325 | 2 | 28 | 2.334.9 ± 1482.7 | 54.8 |
| 12.5 | 5 | 0.3068 ± 0.0250 | 4 | 0.2997 ±0.1758 | 4 | 38 | 3315.1 ± 1425.1 | 35.9 |
| 6.25 | 5 | 0.3469 ± 0.0152 | 5 | 0.1608 ±0.0080 | 4 | 76 | 6993.3 ± 1758.3 | 0 |
| 2.76 | 5 | 0.2875 ± 0.0405 | 5 | 0.1344 ±0.0183 | 5 | 55 | 5297.8 ± 1603.2 | 0 |
| Control | 5 | 0.344 ± 0.0345 | 4 | 0.1026 ±0.0320 | 4 | 73 | 5171.04 ± 1736.0 | — |

The data presented in Tables 1, 2 and 3 indicate that the 1:1 mixture of octadecane and 1-chloroundecane is effective against larvae and replete females of *B. microplus* and nymphs of *A. variegatum*.

EXAMPLE 4

The brown dog tick, *Rhipicephalus sanguineus* was used to test the efficacy of each of the individual components of the present composition. The method of treating was the Koch and Burkwhat test, described above. The results can be seen below in Table 4.

TABLE 4

Acaricidal activities against the brown dog tick *Rhipicephalus sanguineus*

| Candidate | Test Concentraton | % Kill |
|---|---|---|
| Octadecane | 1 | 1 |
|  | 5 | 7.5 |
|  | 15 | 29 |
| 1-Chloroundecane | 1 | 35 |
| 1-Chlorooctadecane | 5 | 90 |
|  | 15 | 70 |
|  | 1 | 22 |
| 1,2-Epoxycyclododecane | 5 | 33 |
|  | 15 | 40 |
|  | 1 | 30 |
| 1-Chlorohexadecane | 5 | 65 |
|  | 15 | 100 |
|  | 1 | 20 |
| 1,2-Epoxyoctadecane | 5 | 15 |
|  | 15 | 50 |
|  | 1 | 77 |
| 1-Chlorotetradecane | 5 | 95 |
|  | 15 | 100 |
|  | 1 | 65 |
|  | 5 | 100 |
| Undecanoic acid | 1 | 90 |
| cis-Oleylamine | 1 | 43 |
|  | 5 | 85 |
|  | 15 | 100 |
| PROLATE (R) | 1 | 100 |

A commercially available, acaricidal product, PROLATE®, was tested to provide a basis of comparison of efficacy with the compounds of the present invention.

The foregoing examples are not intended to limit the scope of the invention. The scope of the invention is defined solely by the appended claims.

We claim:

1. An acaricidal composition comprising acaricidally effective amounts of a combination of two different compounds, wherein the first compound is octadecane and the second compound is selected from the group consisting of 1-chloroundecane, 1-chlorooctadecane, 1-chlorotetradecane, and 1-chlorohexadecane; and an inert chemical carrier.

2. The composition of claim 1 wherein said second compound is 1-chloroundecane.

3. The composition of claim 1 wherein said first and second compounds are mixed in a ratio of about 1:1.

4. The composition of claim 1 wherein said compounds comprise between about 1% and about 15% by weight of said composition.

* * * * *